(12) United States Patent
Ronco et al.

(10) Patent No.: US 8,968,743 B2
(45) Date of Patent: Mar. 3, 2015

(54) METHOD AND COMPOSITIONS FOR CUTANEOUS IMMUNISATION

(75) Inventors: Jorge Ronco, Rambouillet (FR); Sylvie Godefroy, Paris (FR); Bertrand Dupont, Aix en Provence (FR)

(73) Assignee: DBV Technologies, Bagneux (FR)

( * ) Notice: Subject to any disclaimer, the term of this patent is extended or adjusted under 35 U.S.C. 154(b) by 662 days.

(21) Appl. No.: 12/745,673

(22) PCT Filed: Dec. 3, 2008

(86) PCT No.: PCT/FR2008/052198
§ 371 (c)(1),
(2), (4) Date: Jun. 1, 2010

(87) PCT Pub. No.: WO2009/080933
PCT Pub. Date: Jul. 2, 2009

(65) Prior Publication Data
US 2010/0310596 A1    Dec. 9, 2010

(30) Foreign Application Priority Data

Dec. 3, 2007   (FR) ..................... 07 59505

(51) Int. Cl.
  *A61K 39/00*   (2006.01)
  *A61F 13/02*   (2006.01)
  *A61K 9/70*    (2006.01)
(52) U.S. Cl.
  CPC .............. *A61K 9/7084* (2013.01); *A61K 39/00* (2013.01); *A61K 2039/54* (2013.01); *Y10S 977/773* (2013.01)
  USPC ......................... 424/184.1; 977/773; 427/2.31

(58) Field of Classification Search
None
See application file for complete search history.

(56) References Cited

U.S. PATENT DOCUMENTS

| 3,212,495 A | 10/1965 | Osbourn et al. |
| 3,645,852 A | 2/1972 | Axen et al. |
| 3,837,340 A | 9/1974 | Counter |
| 3,894,531 A | 7/1975 | Saunders, Jr. |
| 4,435,180 A | 3/1984 | Leeper |

(Continued)

FOREIGN PATENT DOCUMENTS

| EP | 0 107 832 A2 | 10/1983 |
| EP | A-107832 | * 5/1984 ............. A61K 39/35 |

(Continued)

OTHER PUBLICATIONS

International Search Report for PCT/FR2008/052198, in French and English, mailed May 11, 2009, 6 pages.

(Continued)

*Primary Examiner* — Zachariah Lucas
*Assistant Examiner* — Stuart W Snyder
(74) *Attorney, Agent, or Firm* — Foley & Lardner LLP; Christopher C. Bolten; Nicola A. Pisano

(57) ABSTRACT

The invention concerns the development of a system to deliver vaccines via cutaneous route. The invention more particularly concerns the use of a device comprising a condensation compartment for epicutaneous vaccination. The invention also concerns protocols for epicutaneous vaccination allowing an efficient immune response to be obtained without any skin treatment. The invention can be implemented in any mammal, preferably in human beings, to induce a therapeutic or preventive immune response against any type of antigen.

21 Claims, 10 Drawing Sheets

(56) References Cited

U.S. PATENT DOCUMENTS

| | | | |
|---|---|---|---|
| 4,450,844 A | 5/1984 | Quisno | |
| 4,743,249 A | 5/1988 | Loveland | |
| 4,781,705 A | 11/1988 | Shepherd et al. | |
| 4,788,971 A | 12/1988 | Quisno | |
| 4,821,733 A | 4/1989 | Peck | |
| 4,836,217 A | 6/1989 | Fischer | |
| 5,236,455 A | 8/1993 | Wilk et al. | |
| 5,438,984 A | 8/1995 | Schoendorfer | |
| 5,827,608 A | 10/1998 | Rinehart et al. | |
| 6,093,419 A | 7/2000 | Rolf | |
| 6,142,954 A | 11/2000 | Anhauser et al. | |
| 6,210,705 B1 | 4/2001 | Mantelle et al. | |
| 6,316,598 B1 | 11/2001 | Van Dyke et al. | |
| 7,635,488 B2 | 12/2009 | Dupont et al. | |
| 2002/0102291 A1 | 8/2002 | Mantelle et al. | |
| 2002/0151487 A1 | 10/2002 | Nickoloff et al. | |
| 2002/0168761 A1 | 11/2002 | Gour et al. | |
| 2003/0064088 A1 | 4/2003 | Carvalho et al. | |
| 2004/0047902 A1* | 3/2004 | Dupont et al. | 424/449 |
| 2004/0137004 A1 | 7/2004 | Glenn et al. | |
| 2004/0146534 A1* | 7/2004 | Glenn et al. | 424/257.1 |
| 2006/0002949 A1 | 1/2006 | Glenn et al. | |
| 2006/0147509 A1 | 7/2006 | Kirkby et al. | |

FOREIGN PATENT DOCUMENTS

| | | | |
|---|---|---|---|
| EP | 0 409 465 A2 | 1/1991 | |
| EP | 0 976 396 A1 | 2/2000 | |
| EP | 1 031 346 A1 | 8/2000 | |
| EP | 1 356 821 A2 | 10/2003 | |
| FR | 2 527 450 | 12/1983 | |
| FR | 2 866 553 | 8/2005 | |
| GB | 501873 | 3/1939 | |
| GB | 1013895 | 12/1965 | |
| JP | 06-238008 | 8/1994 | |
| JP | 2000-083580 | 12/1999 | |
| WO | WO 96/32142 | 10/1996 | |
| WO | WO 98/25521 | 6/1998 | |
| WO | WO 98/31315 A1 | 7/1998 | |
| WO | WO 00/61184 * | 4/2000 | A61K 39/39 |
| WO | WO 00/43058 A1 | 7/2000 | |
| WO | WO 00/61184 * | 10/2000 | |
| WO | WO 01/49302 A1 | 7/2001 | |
| WO | WO 02/30281 A1 | 4/2002 | |
| WO | WO 02/071950 A1 * | 9/2002 | A61B 10/00 |
| WO | WO 02/074325 A1 | 9/2002 | |
| WO | WO 02/076379 A2 | 10/2002 | |
| WO | WO 02/089717 A1 | 11/2002 | |
| WO | WO 02/093998 A2 | 11/2002 | |
| WO | WO 2004/030696 A2 | 4/2004 | |
| WO | WO 2004/052425 A2 | 6/2004 | |
| WO | WO 2006/007366 A2 | 1/2006 | |
| WO | WO 2007/122226 A2 | 1/2007 | |

OTHER PUBLICATIONS

Fentanyl Patch, Brand Name: Duragesic Patches, downloaded Jan. 7, 2007, pp. 1-6.

Anthoni et al., "Smad3 signal transducer regulate skin inflammation and specific IgE response in murine model of atopic dermatitis," The Journal of Investigative Dermatology, vol. 127, No. 8, Aug. 2007, pp. 1923-1929.

Polypropylene, retrieved from http://pslc.ws/mactest/pp.htm, 2005, Polymer Science Learning Center, Department of Polymer Sciences, The University of Southern Mississippi, pp. 1-3.

* cited by examiner

METHOD AND COMPOSITIONS FOR CUTANEOUS IMMUNISATION

CROSS-REFERENCE TO RELATED APPLICATIONS

This application is a national-stage filing under 35 U.S.C. §371 of International Patent Application No. PCT/FR2008/052198, filed Dec. 3, 2008, which claims the benefit of French Patent Application No. 0759505, filed Dec. 3, 2007, the entire contents of both of which are incorporated by reference herein.

FIELD OF THE INVENTION

The invention concerns the development of a method and system to deliver vaccines via cutaneous route. The invention more particularly concerns the use of a device comprising a condensation compartment for epicutaneous vaccination. The invention also concerns protocols for epicutaneous vaccination allowing to obtain an efficient immune response without any skin treatment. The invention can also be used in any mammal, preferably in human beings, to induce a therapeutic or preventive immune response against any type of antigen.

DESCRIPTION OF RELATED ART

The majority of pathogens enter the body via the mucosa or the skin. The skin, like the mucosa, therefore has all the necessary tools to detect pathogens and to defend itself. This line of defence notably comprises a contingent of professional, resident antigen-presenting cells (APCs). The only APCs present in the epidermis under normal conditions are the Langerhans cells (LC), dendritic cells (DC) derived from bone marrow. After capturing the antigen, the activated LCs migrate into the draining lymphatic glands where they initiate a powerful systemic immune response. The skin therefore represents a potential alternative to the route of administration via traditional injection for the development of more efficient vaccines. In addition, the skin's immunity system can also be an ideal target for the induction of tolerance in different pathologies such as auto-immune diseases, allergies and possibly cancer.

However, the stratum corneum (SC), the topmost skin layer, is an effective physicochemical barrier against the entry of fluids, of large molecules (polypeptides and proteins), of particles or even microbes. A variety of techniques have been tested to endeavour to obtain an efficient immune response via epicutaneous route i.e. by application of an antigen to the skin. These techniques all involve physical deterioration of the stratum corneum, for example by slight or moderate abrasion (subsequent to the application of adhesive strips or using sandpaper), by applying ultrasound or micro-needles. These different techniques have shown efficacy, to a greater or lesser extent, as prior step before application of the antigen, to promote its entry into the surface layers of the skin (epidermis), containing the immunological cells, and the induction of an immune response. It has been shown for example that the co-application of an antigen and of an adjuvant such as the cholera toxin (CT) or labile toxin of E. coli (LT) to previously abraded skin is efficient in generating an immune antibody response (Glenn G M, Rao M, Matyas G R, Alving C R. Skin immunization made possible by cholera toxin. Nature. 1998. 391: 851; Glenn G M, Scharton-Kersten T, Vassell R, Matyas G R, Alving C R. Transcutaneous immunization with bacterial ADP-ribosylating exotoxins as antigens and adjuvants. Infect Immun. 1999. 67:1100-6.). On the other hand, mere hydration of the skin before applying an antigen, whether or not followed by occlusive treatment, has never given rise to a specific antibody response. This is solely obtained if the skin is previously treated, leading to physical perturbation of the stratum corneum, or if the antigen is co-administered with a powerful adjuvant (CT or LT).

Other work has subsequently shown that the use of an occlusive system to hold in place a vaccine formulation, deposited in liquid form on the skin of animals for a period ranging from 1 to 24 hours, allowed the inducing of an immune response in animals and in man but solely after treatment of the skin. However, the induced responses using a contact period of 0 to 24 hours do not vary qualitatively and/or quantitatively.

In WO 2004/03069 application, it was envisaged to induce an immune reaction by means of a composition containing an antigen and an immunostimulatory compound, in dry form, using a PosIntro or ISCOM system.

The use of dermal patches to obtain an immune reaction has also been proposed in international application WO 2007/122226.

Therefore, without any prior physical or physicochemical treatment (sandpaper, ethanol, acetone, adhesive strip, glycerol) or the use of powerful adjuvants (LT or CT) or other facilitating excipient, no antigen-specific antibody response is detected.

SUMMARY OF THE INVENTION

The present invention, for the first time, describes a method enabling the induction of an antigen-specific immune response via cutaneous route, without the need to use an adjuvant (CT or LT) or to pre-treat or perforate the skin. More particularly, the invention describes a method for epicutaneous vaccination that is efficient even in the absence of any adjuvant, which is based on the use of a dry vaccine formulation applied to the skin under conditions allowing the formation of a condensation compartment. The invention shows that the creation and maintaining of skin hydration leads to perturbation of the SC allowing the passing of antigens. In addition, the water accumulated under the delivery system allows the dry vaccine formulation to be rehydrated and solubilised and to enter into contact with the skin. We have shown in pre-clinical trials that, contrary to the different cutaneous systems described up until now, the invention allows to induce an immunogen-specific antibody response without the co-administering of any adjuvant (of CT or LT type) and without any skin preparation (abrasion or perforation). In particularly noteworthy manner, the invention enables the cutaneous transfer of macro-molecules (chiefly polypeptides and proteins) without any active treatment, which has never been described in the prior art. As illustrated in the examples, a particularly strong immune response is observed after three applications of the vaccine using the method of the invention.

One object of the invention therefore resides in the use of a vaccine formulation to prepare a composition for epicutaneous vaccination of a mammal, preferably a human, characterized in that the vaccine formulation is in dry form devoid of any adjuvant, and in that it is administered by application to the skin of the mammal by means of a cutaneous device which, in contact with the skin, forms a condensation compartment containing the vaccine formulation.

A further object of the invention resides in the use of a cutaneous administration device to prepare a composition intended for the administration of a vaccine formulation containing an antigen, without any prior treatment of the skin or any co-administering of an adjuvant, the cutaneous administration device containing the vaccine formulation in dry form without an adjuvant compound and, when in contact with the skin, totaling a condensation compartment containing the vaccine formulation, thereby enabling the entry of the antigen into the epidermis and the induction of an immune response in the absence of any adjuvant or prior treatment of the skin.

A further object of the invention resides in the use of a cutaneous administration device to administer a vaccine formulation containing an antigen, without any prior treatment of the skin or co-administering of an adjuvant, the cutaneous administration device containing the vaccine formulation in dry form without an adjuvant compound and forming a condensation compartment in contact with the skin, which contains the vaccine formulation, thereby enabling the entry of the antigen into the epidermis and the induction of an immune response without an adjuvant or any prior treatment of the skin.

A further object of the invention resides in a method to induce an antigen-specific immune response in a mammal, the method comprising the application to the skin of the mammal, without any prior skin treatment, of a cutaneous administration device containing a vaccine formulation in dry form including the antigen without any adjuvant compound, the device forming in contact with the skin a condensation compartment containing the vaccine formulation, the application time being sufficient to allow the entry of the antigen into the epidermis and the induction of an immune response without an adjuvant or prior treatment of the skin.

A further object of the invention resides in a method to induce an antigen-specific immune response via cutaneous route, the method comprising the creation and maintaining of local skin hydration and contacting of the hydrated skin with a dry, adjuvant-free vaccine formulation for a sufficient time to allow the entry of the antigen and the induction of an immune response.

A further object of the invention relates to a method to induce a systemic immune response against a protein antigen in a subject, the method comprising the administering of said antigen to said subject via epicutaneous route by means of a skin device comprising a backing, the peripheral part of said backing being adapted to create a hermetic chamber with the skin, wherein the backing holds said antigen on its face in contact with the skin, inside the chamber, said antigen being removed from the backing after application of the device to the skin and then delivered to the subject via epicutaneous route, said administration leading to the induction of a systemic immune response in the subject.

In one particular embodiment, the peripheral part of the backing of the cutaneous device has adhesive properties on wet skin.

In another embodiment of the invention, the systemic immune response induced after administration of an antigen by means of a cutaneous device includes a humoral response.

In one preferred embodiment, condensation is formed inside the chamber after application of the cutaneous device to the skin, said condensation causing or increasing the movement and epicutaneous delivery of the antigen. In particular, this condensation can be formed by perspiration.

A further object of the invention concerns a method to induce a systemic immune response against a protein antigen in a subject, wherein said antigen is in dry form or particle form. More particularly, the antigen can be attached to the support without an adhesive by means of electrostatic forces and/or Van der Waals forces, or by means of an adhesive coating on the support.

Preferably, the antigen can be applied to the support by means of a spraying/drying method. Said antigen can also be dissolved or dispersed in a liquid, in which case it is held on the support in a reservoir of adsorbent material.

A further object of the invention concerns the use of a vaccine formulation in dry form to prepare a medicinal product for the induction of an immune response in a mammal, characterized in that the vaccine formulation is applied by means of a cutaneous device without any adjuvant compound to the non-treated skin of a mammal, for a period of about 48 hours.

A further object of the invention concerns the use of a vaccine formulation in dry form for the induction of an immune response in a mammal, characterized in that the vaccine formulation is applied by means of a cutaneous device without an adjuvant compound to the non-treated skin of the mammal, for a period of about 48 hours.

A further object of the invention concerns a method to induce an immune response in a mammal, comprising the application of a vaccine formulation in dry form, by means of a cutaneous device free of adjuvant compound to the non-treated skin of a mammal, for a period of about 48 hours.

A further object of the invention concerns a cutaneous device comprising a backing, the peripheral part of said backing being adapted to create a hermetic chamber with the skin, wherein the backing holds said antigen on its face in contact with the skin, inside the chamber, said antigen being removed from the backing after application of the device to the skin and then delivered to the subject via epicutaneous route.

A further object of the invention concerns a vaccine composition, characterized in that it comprises a cutaneous administration device forming a condensation compartment after application to the skin of a subject, said compartment comprising a vaccine formulation in dry form free of any adjuvant compound.

DETAILED DESCRIPTION

The invention results from the unexpected discovery that an immune response can be induced via cutaneous route on an intact skin (i.e. not previously perforated or physically and/or chemically abraded) and without the use of an adjuvant. This effect was obtained using a vaccine formulation in dry form and applying it by means of a device forming a condensation compartment when applied to the skin and/or for an adapted period of time.

Without being restricted to any particular mechanism of action, it is proposed that hydration of the skin allows swelling of the corneocytes of the stratum corneum and the integration of water molecules between the lipid domains of the intercellular spaces. This hydration would also induce perturbation of cutaneous homeostasis, resulting inter alia in changes of the profile of the cytokines produced, in morphological and phenotypic changes of the Langerhans cells or in an increase in the number of epidermal mononuclear cells.

Despite the skin's barrier role, a flow of water directed towards the atmosphere is set up through the skin between the body and the atmosphere, under physiological conditions. This flow is known under the name Insensible Water Loss (IWL). The method of the invention, which uses a condensation compartment, contributes towards isolating part of the skin from the surrounding medium. During this phenomenon, exchanges of water vapour between the body and the atmosphere are disturbed, which would lead to the accumulation of water in the compartment and also to increased hydration of the skin, of the entire epidermis and in particular of the stratum corneum which forms the main barrier against the absorption of substances. Our results suggest that in humans, the very strong flow of water measured after removal of the condensation compartment reflects the evaporation of water accumulated on the skin surface. The condensation compartment of the device, over time, leads to water vapour saturation (derived from IWL) of the volume of the compartment, then to condensation, reaching a state of equilibrium. At the beginning of application, this volume is not saturated with water vapour, since it contains ambient air. Once saturation of the atmosphere is reached, the water in vapour state could then condense into liquid water form. This condensation may be fed by the flow of residual water from the skin. Under these conditions, a state of equilibrium is reached which results in the accumulation of water underneath the watertight device (see FIG. 1B).

The invention can therefore solve the disadvantages of prior art epicutaneous vaccination methods, by proposing a method which can be used with any type of antigen, compatible with the production of ready-to-use devices and not requiring any skin treatment. The strong hydration induced in the epidermis, with accumulation of water in and on the surface of the stratum corneum, makes it possible to modulate the partition coefficient between the vaccine molecules and the skin in the presence of water, to swell the corneocytes or to disrupt the organisation of the intercellular lipid phase. This modification allows dissolution of the active ingredient in the liquids present on the skin surface and its entry (via passive diffusion) through the skin without it being necessary to perforate or abrade the skin.

The invention can be implemented with any cutaneous administration device forming a condensation compartment. This is preferably a device of patch or dressing type, preferably patches. The device of the invention is typically of transdermal type with passive diffusion i.e. it does not contain means to cause perforation or abrasion of the skin. It is advantageously a device of occlusive patch type such as an electrostatic patch produced using VIASKIN® technology described in patent application WO 02/071950.

In the meaning of the invention, the term "compartment" designates the space left between the skin and the backing of the device after application of the device onto the skin, this backing not adhering to the skin and thereby leaving room for the accumulation of a small quantity of water on the skin (see for example FIGS. 1A and 1B). The results obtained show that the use of a condensation compartment which, during the time of application, maintains a certain extent of hydration due to the natural expressing of liquid by the skin in the direction of the compartment, allows the passing of macromolecular antigens and the induction of a specific response. These results are particularly surprising having regard to prior art data which stress the need to have recourse to particular adjuvants and to treatment of the skin to obtain a satisfactory response.

In one preferred embodiment, the device is such that, in contact with the skin, it forms a condensation compartment having a volume of between 1 and 300 mm$^3$ per cm$^2$ of surface of the device. Said volume corresponds to a compartment height of about 0.01 mm to 3 mm. In one preferred embodiment, the volume of the compartment is comprised between 2 and 200 mm$^3$ per cm$^2$ of surface of the device, or more preferably between 2 and 100 mm$^3$ per cm$^2$ of surface of the device, corresponding to a height of about 0.02 to 1 mm. The diffusion surface on the skin of the device can be adapted by the person skilled in the art, and is typically between about 0.2 and 5 cm$^2$, more generally between 0.5 and 3 cm$^2$.

It is not necessary for the walls of the condensation compartment (the backing of the device) to be fully impervious. On the contrary, certain permeability to water vapour under normal temperature and pressure conditions is acceptable, as is the case with polyethylenes, provided that this evaporation does not prevent the maintaining of a saturated water vapour atmosphere through the presence of liquid water in the compartment.

In one particular embodiment, the walls of the condensation compartment comprise a material having a permeability rate of less than 15 g/m$^2$/24 h, preferably less than 10 g/m$^2$/24 h, for example in the order of about 9 g/m$^2$/24 h.

Said materials can be chosen for example from among polymers, copolymers, plastics, ceramic, any biocompatible material (e.g. graphite), etc. Examples of biocompatible polymers are notably polyethylene (PE), polycarbonate, polyester (PET), cellulose plastics (CA, CP), polyvinyl chloride (PVC), polymethyl-methacrylate (PMMA), polyurethane (PUR), silicones (PTFE) or polyvinylidene fluoride (PVDF). One example of a biocompatible copolymer is notably the ethylene-vinyl acetate copolymer (EVA).

As examples of polymers having moisture vapour transmission rates (MVTRs) compatible with the present invention, mention may notably be made of CoTran® 9706 (MVTR=26.4 g/m$^2$/24 h), CoTran® 9720 (MVTR=9.4 g/m$^2$/24 h) and CoTran® 9722 (MVTR=7.9 g/m$^2$/24 h).

In one preferred embodiment, the condensation compartment is formed by a polymer disk e.g. in polyethylene, of essentially circular shape (the backing) and of diameter between about 2 and 100 mm, preferably between about 5 and 70 mm, which is fixed (e.g. glued) onto a ring of biocompatible material, in polyethylene for example, having an outer diameter essentially identical to the outer diameter of the disk and an inner diameter of between 1 and 50, preferably between about 2 and 20 mm. The thickness of the disk and of the ring are between about 0.01 et 2 mm for example, which defines a compartment height of between 0.01 and 2 mm, the volume of the compartment being small but never null, even if the flexibility of the backing, at certain points, defines contact thereof with the skin. The disk can be fixed to the ring by any suitable means. Typically, the ring is adhesive or made adhesive to allow its attachment to the disk.

As illustrated FIG. 1A, one particular prototype of the device according to the invention consists of:

a ring [1] of biocompatible material of variable diameter and height of about 0.01 to 2 mm, depending on the volume of the condensation compartment per cm$^2$ of surface. In the embodiment shown in FIG. 1A, the ring is adhesive at least on its outer face intended to come into contact with the skin;

a disk [2] in biocompatible material, acting as ceiling for the compartment (containing the active ingredient in dry form), attached to the ring (for example by means of an adhesive). The surface of the disk is typically at least 5 mm in diameter. The MVTR (Moisture Vapour Transmission) of the disk (backing) is preferably less than 10 g/m$^2$/24 h.

a release liner [3] protecting the adhesive surface of the ring is intended to be peeled off before application to the skin. This liner is advantageously a disk which covers the compartment so that it is sealed before application of the device.

The compartment formed by the device is a condensation compartment having hydrating properties. A hydrating property results in the capacity to act on the integrity of the epidermis underneath the condensation compartment of the device inducing an increase in the hydration rate of the epidermis, advantageously right from the first hour of application on the skin, ranging from 30% to 100% and more precisely from 50% to 70%. Preferably, the hydrating property of the condensation compartment must be such that, on the outer surface of the epidermis and in the condensation compartment of the device, it allows the inducing of an increase in the relative quantity of water ranging from 40% to over 100% from the first hour of application, and further preferably of more than 50%.

In one preferred embodiment, the device is held to the skin by means ensuring watertightness of the condensation compartment. Any adhesive means can be used for this purpose, including materials of gum, polymer or plastic type having strong adhesive properties.

The invention has the advantage of allowing vaccination even on intact skin i.e. skin which has not previously undergone any particular treatment. In the meaning of the invention, "treatment of the skin" designates any abrasive or perforating treatment leading to at least partial destruction of at least the surface layer of the skin.

Also, a further advantage of the invention is that it allows to obtain a major immune response, even without the co-administering of an adjuvant. In the meaning of the invention, the term "adjuvant" designates any compound which has a physicochemical and/or biological action on the skin, facilitating entry of the antigen into the skin, and which increases the immune response against the antigen. Through physicochemical and/or biological action, the adjuvant such as defined herein is a compound which deteriorates the permeability of the epidermis by perturbing the stratum corneum, thereby enabling the passing of the antigen and its contacting with the immunologically active cells of the epidermis. Examples of adjuvant compounds are notably the cholera toxin (CT) or LT toxin (heat-labile toxin of *E-coli*). Other examples are the transfersomes described by Paul et al (Paul A, Cevc G, Bachhawat B K. Transdermal immunization with large proteins by ultradeformable drug carriers. Eur J Immunol. 1995, 25 (12):3521-4), which enable the transport of an antigen into the membranes.

The invention can be implemented with any vaccine formulation in dry form. The term "vaccine formulation" designates any formulation containing antigen elements. It is typically a formulation containing one or more antigens e.g. of peptide, polypeptide (or protein), lipid and/or saccharide type, or simple mixtures or the chemical conjugates of these compounds. One preferred vaccine formulation comprises one or more antigen molecules: molecules with a molecular weight of more than 500 Da, most often polypeptides and proteins of more than 1,500 Da having a preventive or therapeutic vaccine activity or purpose, or molecules with a molecular weight of more than 500 Da intended for local (therapeutic) action on the epidermis. Typically, the vaccine formulation contains at least one antigen of peptide or polypeptide type. For example, it may be a bacterial antigen, viral antigen, tumour antigen, etc. such as an antigen of the Flu virus, an antigen of the Hepatitis virus (/or C), an antigen of *Haemophilus Influenzae*, an antigen of the respiratory syncytial virus, an antigen of *Salmonella* (Shigella), or of tuberculosis (Tiphy), or antigens characteristic of auto-immune diseases, cancer, Alzheimer's disease, allergies, etc. The vaccine formulation may also contain an excipient or vehicle adapted for pharmaceutical use, or any compound with immunomodulatory activity such as a cytokine, a ligand compound of the Toll receptors, etc.

The vaccine formulation is used in "dry form", i.e., in dehydrated form and notably a powder, particle, agglomerate, cake, dried form, etc. The dry form can be obtained by freeze-drying or by simple evaporation.

In one particular embodiment, the vaccine formulation is in powder form.

In another particular embodiment, the vaccine formulation is held on a surface of the device, typically on the backing of the compartment, by chemical or physicochemical forces if there is no adhesive material on this surface. Preferably, the vaccine formulation is held on a surface of the device, typically on the backing of the compartment, by electrostatic forces or by Van der Waals forces.

In one normal embodiment, the device contains a quantity of vaccine formulation of between 0.1 $\mu g/cm^2$ and 500 $\mu g/cm^2$, preferably between 20 $\mu g$ and 300 $\mu g$ per $cm^2$, further preferably between 20 $\mu g$ and 100 $\mu g$ per $cm^2$. It is to be understood that this quantity can be adapted by the person skilled in the art in relation to the objectives, pathology, duration of treatment, subject, etc.

The invention enables a significant immune response to be induced, even in the absence of an adjuvant and skin treatment. The invention can be used for preventive or therapeutic vaccination against any type of pathogen (virus, parasites, bacteria, proteins, etc.), against tumour cells or against self antigens, or for the treatment of allergic individuals. The results given show the inducing of an antigen-specific response, notably a response of IgG type antibodies.

The amplitude of the immune response can be adapted by modifying the application time of the device, and/or by conducting repeat applications. As is illustrated in the examples, the induced immune response after three applications of the vaccine for only 6 hours, is equivalent to that observed for an application time of 24 hours (Example 2). We have shown, for example, that hydration maintained for periods ranging from 6 hours to 24 hours is sufficient to develop an immune response, even without prior treatment of the skin and without the co-administering of an adjuvant.

Additionally, we also extended the period of application to 48 and 72 hours (Example 5). The results obtained show that the time of 48 hours gives surprising results since the antibody-specific response increases by almost one magnitude compared with the application time of 24 hours. An application that is continued beyond 48 hours, for example an application time of 72 hours, does not appear to contribute towards further increasing the antibody response.

In one preferred embodiment, the invention comprises the successive application to the subject of at least two devices, preferably at least three, each application being spaced apart by about 7 to 30 days, preferably by 10 to 20 days, typically by about 15 days.

Preferably, for each application, the device is held on the skin for a period of about 6 to 72 hours, preferably about 6 to 48 hours, further preferably for about 48 hours.

One particularly preferred protocol to induce an immune response comprises at least three successive applications of a device for a period of about 48 hours, each application being spaced apart by about 15 days.

In the foregoing, the expression "about" designates a variation of ±10% compared with the given value.

The invention also shows that a major antibody response is obtained by epicutaneous vaccination on intact skin when the vaccine formulation is in dry form and is applied for one or more periods of about 48 h, preferably for repeated periods of about 48 h.

The invention can be used for vaccination against any antigen in any mammal. It can be used in children or adults and is essentially non-invasive, and does not require the use of adjuvants.

Other aspects and advantages of the present invention will become apparent on reading the following examples which are to be considered as illustrative and non-limiting.

EXAMPLES

Example 1

Preparation of a Cutaneous Device Containing a Condensation Compartment

Figure 1:
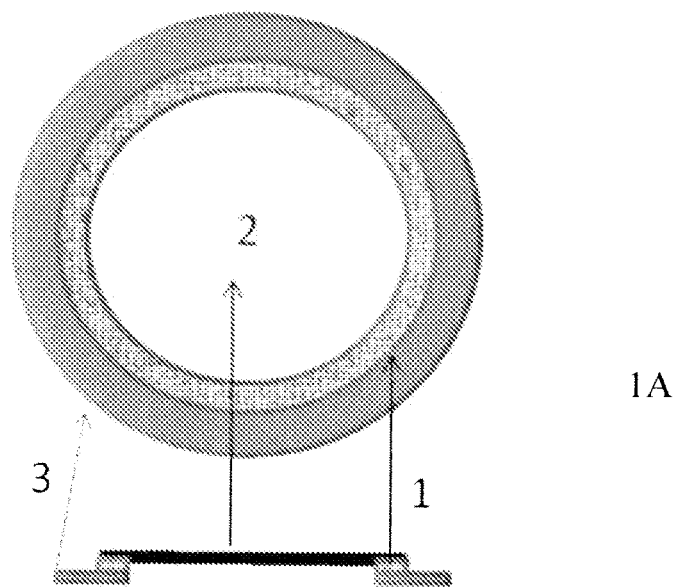
FIG. 1: A—Schematic of the cutaneous device with condensation compartment: [1] ring of biocompatible material, [2] "backing" disk adhering by means of a double-sided adhesive on the disk, [3] release liner to be peeled off before application and protecting the adhesive. B—Schematic of water vapour flows in the condensation compartment.
Figure 1:
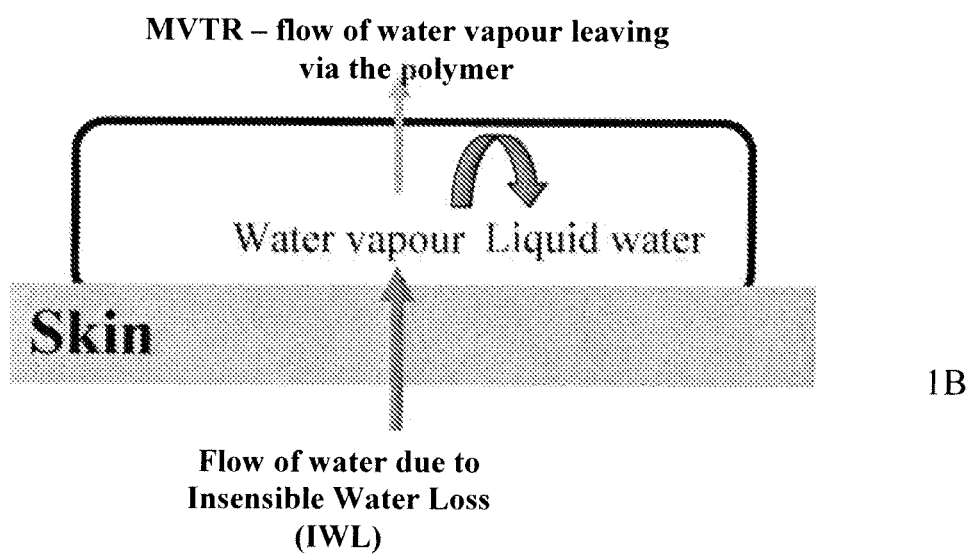

Cutaneous application devices having a condensation compartment were prepared using as backing a polyethylene film (3M) coated with a ring of foam imparting the desired height to the compartment, made adhesive on both its sides (thickness=0.7 mm). This device therefore has a diffusion surface on the skin of 1 cm$^2$ and an expansion compartment for air diffused through the skin of 70 mm$^3$ (see FIG. 1A).

Several polymers having different Moisture Vapour Transmission Rates (MVTRs) were used, notably CoTran® 9706 (MVTR=26.4 g/m$^2$/24 h), CoTran® 9720 (MVTR=9.4 g/m$^2$/24 h) and CoTran® 9722 (MVTR=7.9 g/m$^2$/24 h).

Example 2

Figure 2:
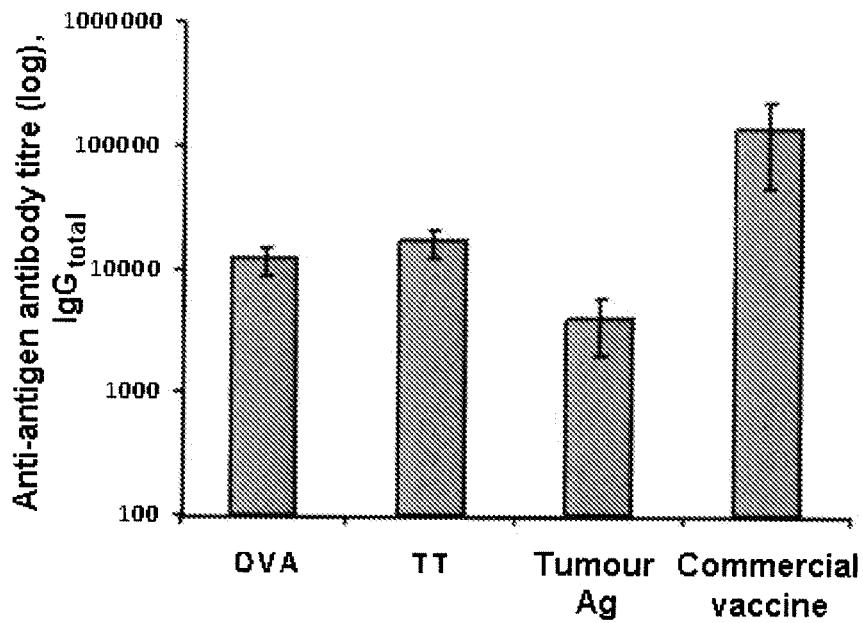
FIG. 2: Induction of an antigen-specific antibody immune response via epicutaneous route on an intact skin without the co-administering of adjuvants using a device comprising a condensation compartment.

Induction of an Antigen-Specific Antibody Immune Response Via Epicutaneous Route, without any Adjuvant Compound Nor any Perforating or Abrasive Skin Treatment Cutaneous administration devices containing a condensation compartment, prepared following Example 1 but with a volume of 10 mm$^3$/cm$^2$ containing an ovalbumin model antigen (OVA), tetanus toxin (TT), tumour antigen or a commercial anti-influenza vaccine, in dry form, were applied for 24 hours to the backs of female BALB/c mice (n=6 to 10), shaven and depilated the day before the applications. The applications were renewed at 2 and 4 weeks after the first. The anti-antigen total IgG-type antibodies were assayed by ELISA on the sera of animals sampled 2 weeks after the last application. The results given in FIG. 2 are expressed in antigen-specific antibody titre. For the serum of each animal, this is the inverse of the dilution at which absorbance measured at 450 nm is equal to the cut-off value determined on the sera of naïve mice. The results obtained show the induction of a strong antigen-specific immune response, even though no adjuvant was used.

Example 3

Figure 3:
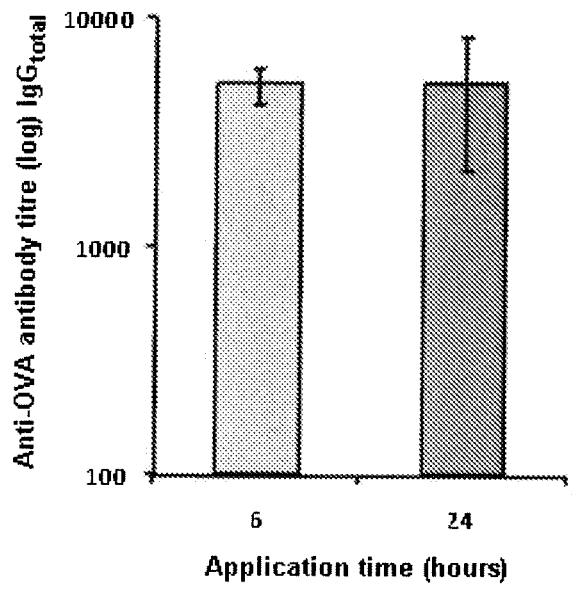
FIG. 3: Induction of an anti-ovalbumin antibody immune response via epicutaneous route after 6 h or 24 h application to the skin of a device comprising a condensation compartment.

Induction of an Anti-Ovalbumin Antibody Immune Response via Epicutaneous Route without an Adjuvant Compound after 6 or 24 h Application to an Intact Skin Cutaneous administration devices comprising a condensation compartment, prepared according to Example 1 but with a volume of 10 mm$^3$/cm$^2$ containing OVA (100 μg) in dry form were applied for 6 or 24 hours to the backs of female BALB/c mice (n=10), shaven and depilated the day before the applications. The applications were renewed at 2 and 4 weeks after the first. The anti-antigen total IgG-type antibodies were assayed using ELISA on the sera of animals sampled 2 weeks after the last application. The results shown in FIG. 3 are expressed as antigen-specific antibody titre. For the serum of each animal, this is the inverse of the dilution at which absorbance measured at 450 nm is equal to the cut-off value determined on the sera of naïve mice. The results obtained show the induction of a strong antigen-specific immune response with application times of 6 or 24 hours.

Example 4

Study of the Quantity and Physical State of Water Available in the Condensation Compartment The skin allows a physiological quantity of water vapour to evaporate. This evaporation is expressed as the Insensible Water Loss—IWL. It causes an increase in the quantity of water vapour in the condensation compartment. The increase in the quantity of vapour in turn causes an increase in the partial water vapour pressure inside the compartment. Starting from a pressure of 53.75 mbar at 35° C., the compartment is in saturated condition. Beyond this pressure, the vapour condenses to liquid water which is deposited on the surface of the skin and is able to fill the condensation compartment. Also, in the composition of the condensation compartment, the polymer of the backing used in this example is not fully impermeable and allows a certain quantity of vapour to escape defined by its Moisture Vapour Transmission Rate (MVTR).

Therefore, in this system, there is equilibrium between firstly the quantity of water entering the compartment in the form of water vapour and secondly the quantity leaving the compartment either via transmission through the polymer film or by condensation. These different quantities were evaluated as follows:

$Q_1 = IWL*S*t$
$Q_2 = MVTR*S'*t$
$Q = Q_1 - Q_2$
$P = nRT/V$ in which $Q_1$=mass of vapour at any time entering the compartment; $Q_2$=quantity of water vapour escaping from the polymer; Q=quantity of water vapour remaining in the compartment; P=pressure in the compartment; S=release surface of water vapour through the skin; S'=release surface of water vapour through the polymer; t=time.

The quantities of water before and after 20 hours' application of the condensation compartment were assessed by IWL measurements on the skins sampled from the backs of hairless rats. The determinations were made by comparison with the areas of skin non-subjected to the device. The skin fragments were mounted on Franz diffusion cells. In the receiver compartment, a PBS buffer pH=7.4 is used to maintain the skin in a state of hydration comparable with the physiological state. When the Franz cells are ready, they are placed in a hot water bath at 37° C. and kept therein for two hours before any other handling operations, so as to equilibrate the temperature with the temperature of physiological flows.

Figure 4:
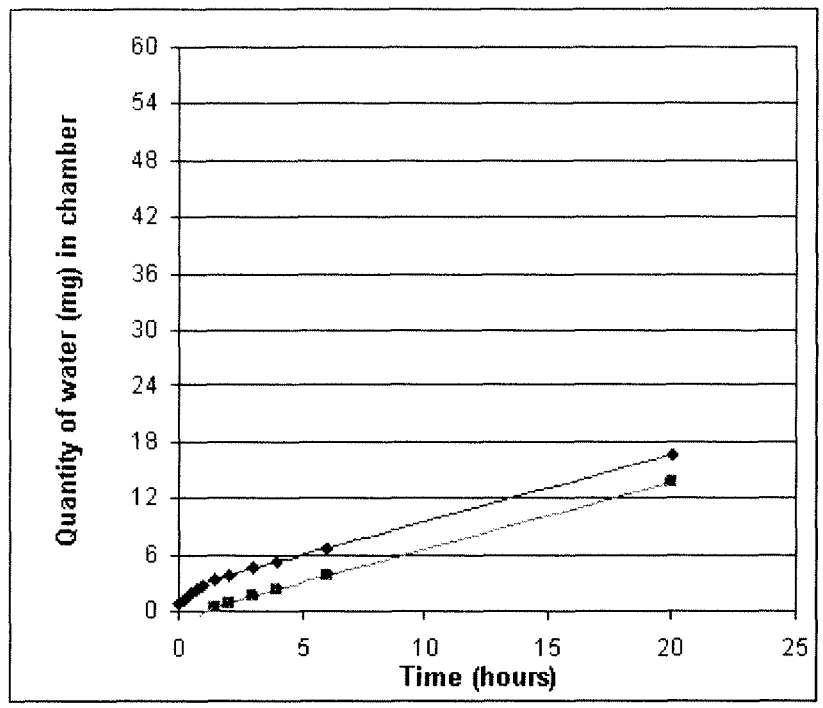
FIG. 4: Ratio between the quantity of water vapour entered the compartment and the quantity of condensed water as a function of time: ■ quantity of water accumulated in the compartment, and ♦ quantity of condensed water in the compartment. ☐ Quantity of water in vapour state after 20 h. ▨ Quantity of water vapour which has condensed after 20 h.

The results given in FIG. 4 show that the water added in vapour form to the compartment starts to condense fairly rapidly after application of the device. According to these results, which express the initial and final data of the system, the quantities of water vapour and liquid water calculated after 20 hours are respectively 1.08 mg/cm² liquid water and 0.3 mg/cm² in the form of water vapour. On visual examination during the experiment, the water appears to accumulate in liquid form on the surface of the skin.

Example 5

Increase in Hydration Percentage of the Different Layers of the Epidermis (Upper, Upper and Medium, Whole Epidermis) Over Time after Application of the Device with Condensation Compartment The Hydrascan® is a device to measure the hydration of the epidermis, developed by Dermscan®. The measuring principle is based on transient thermal transfer (TTT): a constant heat pulse is generated by a stimulator close to the thermal detector and is propagated through the epidermis. Each change in skin temperature is proportional to the quantity of water in the skin (Girard P., Beraud A. and Sirvent A.—Study of three complementary techniques for measuring cutaneous hydration in vivo in human subjects: NMR spectroscopy, transient thermal transfer and corneometry—application to xerotic skin and cosmetics.—Skin Research and Technology, 2000, 6: 205-213). Measurements are given in mW/° C. (it is thermal conductance which measures the ability to conduct heat between two points, in relation to the difference in t° between these two points).

This apparatus is able to measure hydration in the epidermis by making a distinction between 3 layers: the upper layer, intermediate layer and deep layer of the epidermis.

Figure 5:
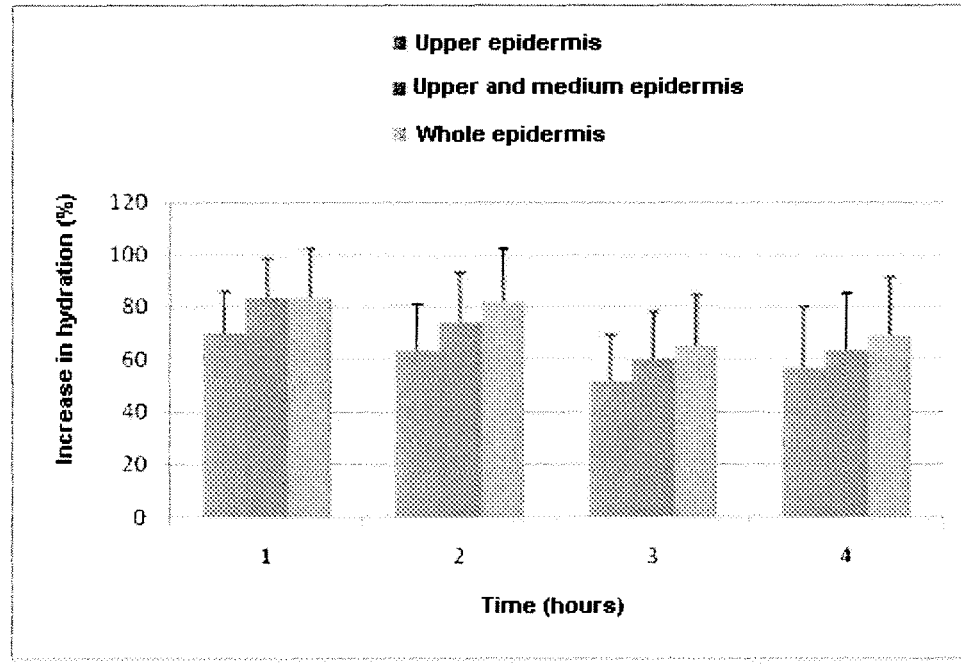
FIG. 5: Increase in the percentage of hydration of the different layers of the epidermis (upper, upper and medium, whole epidermis) in relation to the application time of the device comprising the condensation compartment.

This study was conducted in a group of 15 volunteers: women aged 18-50, Caucasian, normal skin, device with condensation compartment of 70 mm³ applied to the forearm at 28° C. Hydration kinetics was carried out using the Hydrascan measurements at times: 0 h, 1 h, 2 h, 3 h and 4 h. Determinations of hydration of the epidermis underneath the condensation compartment were made at each of these times and compared with determinations on an area of skin not subjected to application of the condensation compartment. The results obtained are given in FIG. 5 and show an increase in hydration rate within the condensation compartment, from the first hour of application, this hydration can be maintained over time.

Example 6

Increase in the Hydration of the Surface of the Skin Over Time, after Application of the Device with Condensation Compartment This study was conducted in a group of 15 volunteers: women aged 18-50, Caucasian, normal skin, device with condensation compartment of 70 mm³ applied to the forearm at 26° C. The determination of Insensible Water Loss (IWL) was made using a Tewameter® 210 (Courage and Khazaka Electronic Gmbh., Köln, Germany).

The determination of the quantity of water accumulated under the condensation compartment, hence on the skin, was calculated using IWL measurements recorded every second for 90 seconds once the device was removed. The areas under curve were calculated for each measurement time. Measurements were taken at 0 h 1 h, 2 h, 3 h and 4 h after application of the condensation compartment.

Figure 6:
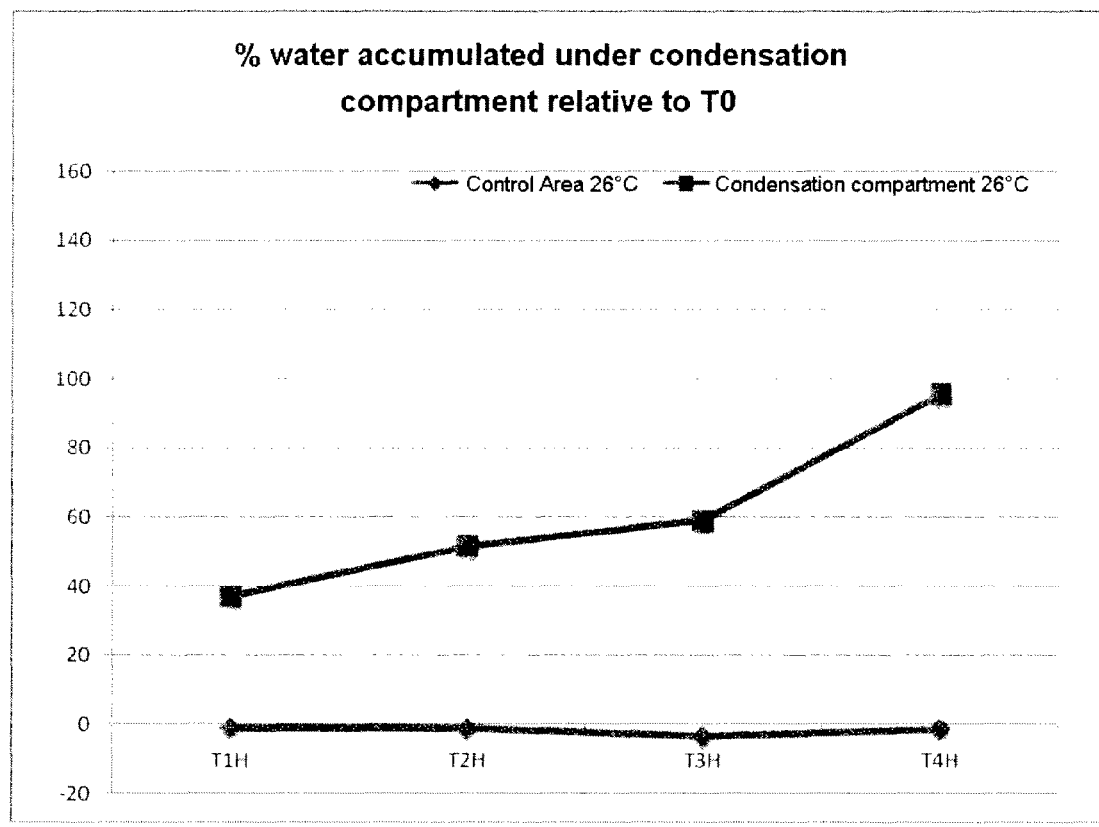
FIG. 6: Increase in the quantity of water accumulated on the surface of the skin in relation to the application time of the device comprising the condensation compartment.

The results obtained are given in FIG. 6 and show an increase in the quantity of water accumulated on the surface of the skin during treatment.

Example 7

Figure 7A:
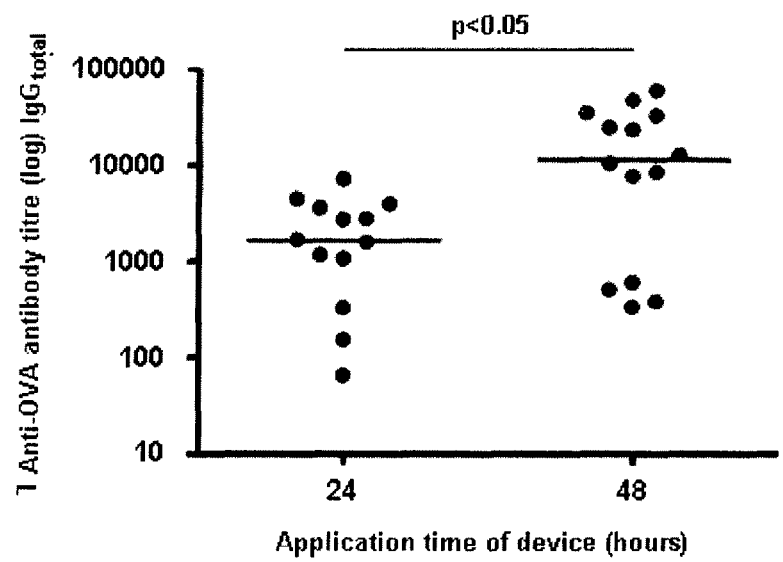
FIG. 7: Potentiation of the anti-ovalbumin antibody immune response, induced by epicutaneous route, by extending the application time to the skin of the device with condensation compartment.
Figure 7B:
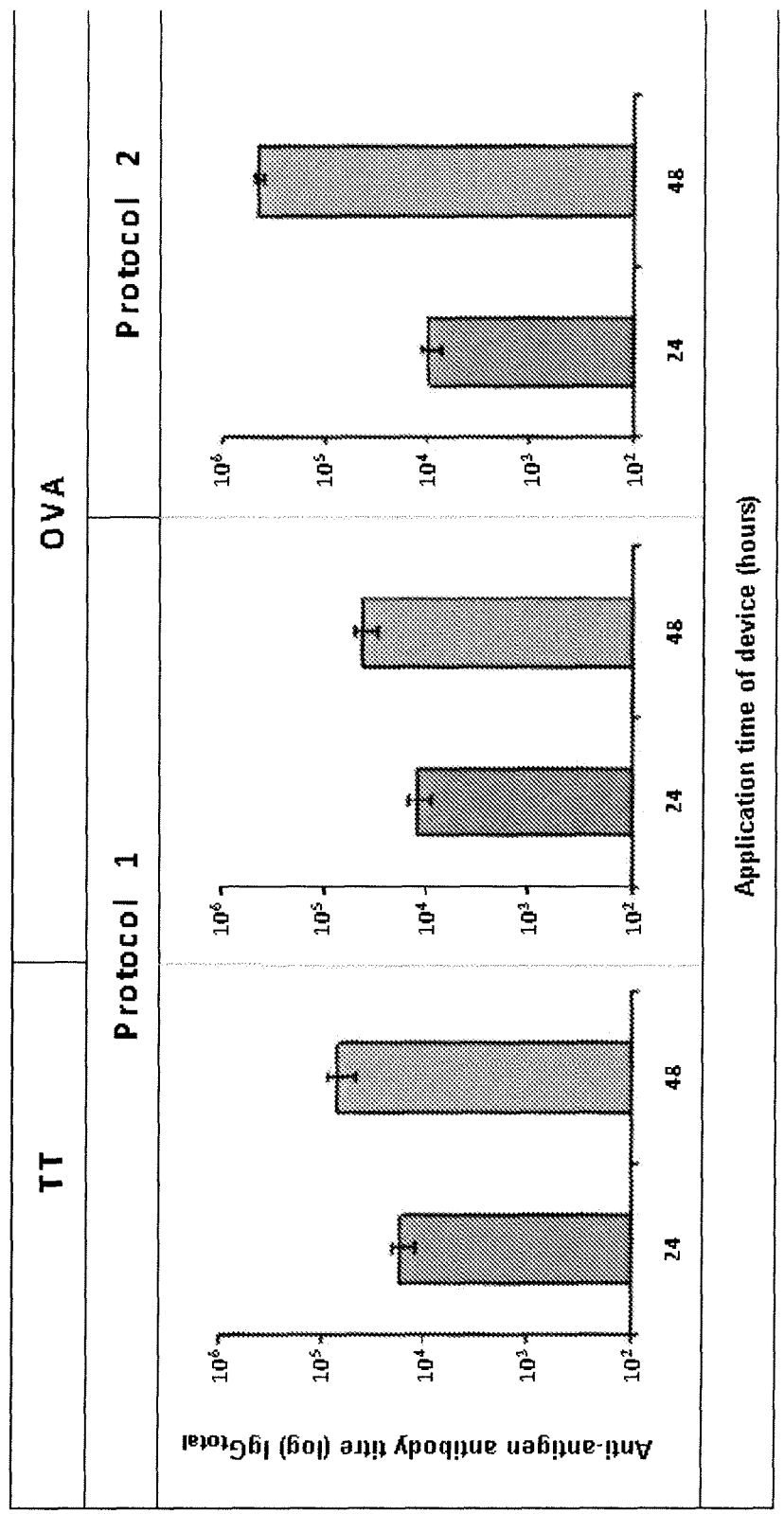

Potentiation of the Anti-Ovalbumin Antibody Immune Response Induced Via Epicutaneous Route, by Extending the Application Time to the Skin Devices containing a condensation compartment, prepared following Example 1 but with a volume of 10 mm³/cm² containing OVA (100 μg) or TT (100 μg) in dry form, were applied for 24 or 48 hours to the backs of female BALB/c mice (n=6 in FIG. 7A, n=10 in FIG. 7B), shaven and depilated the day before the applications. The applications were renewed according to two different regimens:

Protocol 1: at 2 and 4 weeks after the first application (FIGS. 7A and 7B),

Protocol 2: at 2, 7, 9, 14, 21 and 28 days after the first application (FIG. 7B).

The anti-OVA total IgG-type antibodies were assayed by ELISA on the sera of animals sampled 2 weeks after the last application. The results shown in FIGS. 7A and 7B are expressed as antigen-specific antibody titre. For the serum of each animal, this is the inverse of the dilution at which absorbance measured at 450 nm is equal to the cut-off value determined on the sera of naïve mice. The results show a particularly marked antibody-specific response for application times of 48 hours.

Example 8

Figure 8:
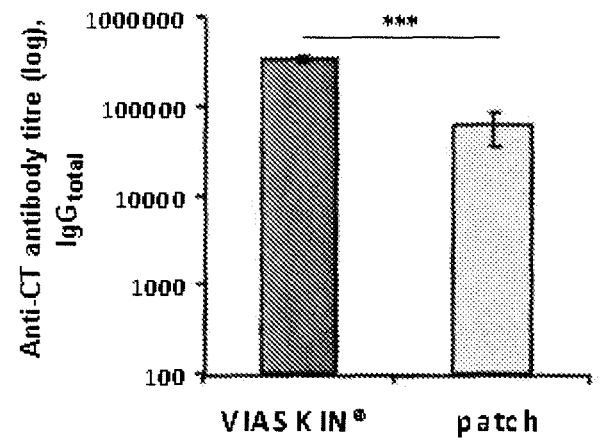
FIG. 8: Induction of a powerful, immunogen-specific antibody immune response via epicutaneous route without any adjuvant or any perforating or abrading treatment of the skin, by comparison with a system of patch type.

Induction of a Powerful Antibody Immune Response Specific to the Immunogen via Epicutaneous Route, without any Adjuvant Compound Nor any Perforating or Abrading Treatment of the Skin, Compared with a Patch Type System Cutaneous administration devices comprising a condensation compartment, prepared following Example 1 but with a volume of 10 mm$^3$/cm$^2$, containing a model immunogen, the cholera toxin (CT), in dry form were applied for 24 hours to the backs of female BALB/c mice (n=10), shaven and depilated the day before the applications. The applications were renewed at 2 and 4 weeks after the first. In addition, systems of patch type composed of gauze on which the immunogen is adsorbed in liquid form, covered by an ordinary adhesive plaster, were applied to the backs of female BALB/c mice under the same conditions as the device described previously. The anti-antigen total IgG-type antibodies were assayed using ELISA on the sera of animals sampled 2 weeks after the last application. The results shown in FIG. 8 are expressed as antigen-specific antibody titre. For the serum of each animal, this is the inverse of the dilution at which absorbance measured at 450 nm is equal to the cut-off value determined on the sera of naïve mice.

The results show the induction of a strong immune response specific to the immunogen when the cutaneous administration with condensation compartment is used, by comparison with the patch-type system.

Example 9

Figure 9:
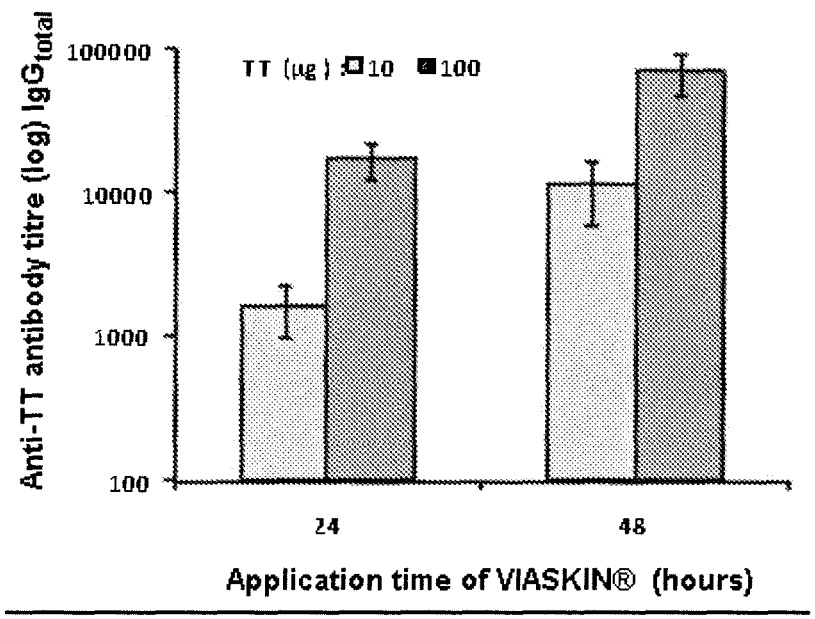
FIG. 9: Induction of anti-TT antibody immune response via epicutaneous route without any adjuvant, with low doses of antigen.

Induction of an Anti-TT Antibody Immune Response via Epicutaneous Route, without an Adjuvant Compound and with a Low Dose of Antigen Cutaneous administration devices comprising a condensation compartment prepared following Example 1 but with a volume of 10 mm$^3$/cm$^2$ containing TT (10 or 100 µg) in dry form, were applied for 24 or 48 hours to the backs of female BALB/c mice (n=10), shaven and depilated the day before the applications. The applications were renewed at 2 and 4 weeks after the first. The anti-antigen total IgG-type antibodies were assayed using ELISA on the sera of animals sampled 2 weeks after the last application. The results shown in FIG. 9 are expressed as antigen-specific antibody titre. For the serum of each animal, this is the inverse of the dilution at which absorbance measured at 450 nm is equal to the cut-off value determined on the sera of naive mice.

The results show the induction of an antigen-specific antibody titre that is equivalent for cutaneous administration devices with condensation compartment containing 100 µg and applied for 24 hours, and for cutaneous administration devices with condensation compartment containing 10 µg and applied for 48 hours.

Example 10

Figure 10:
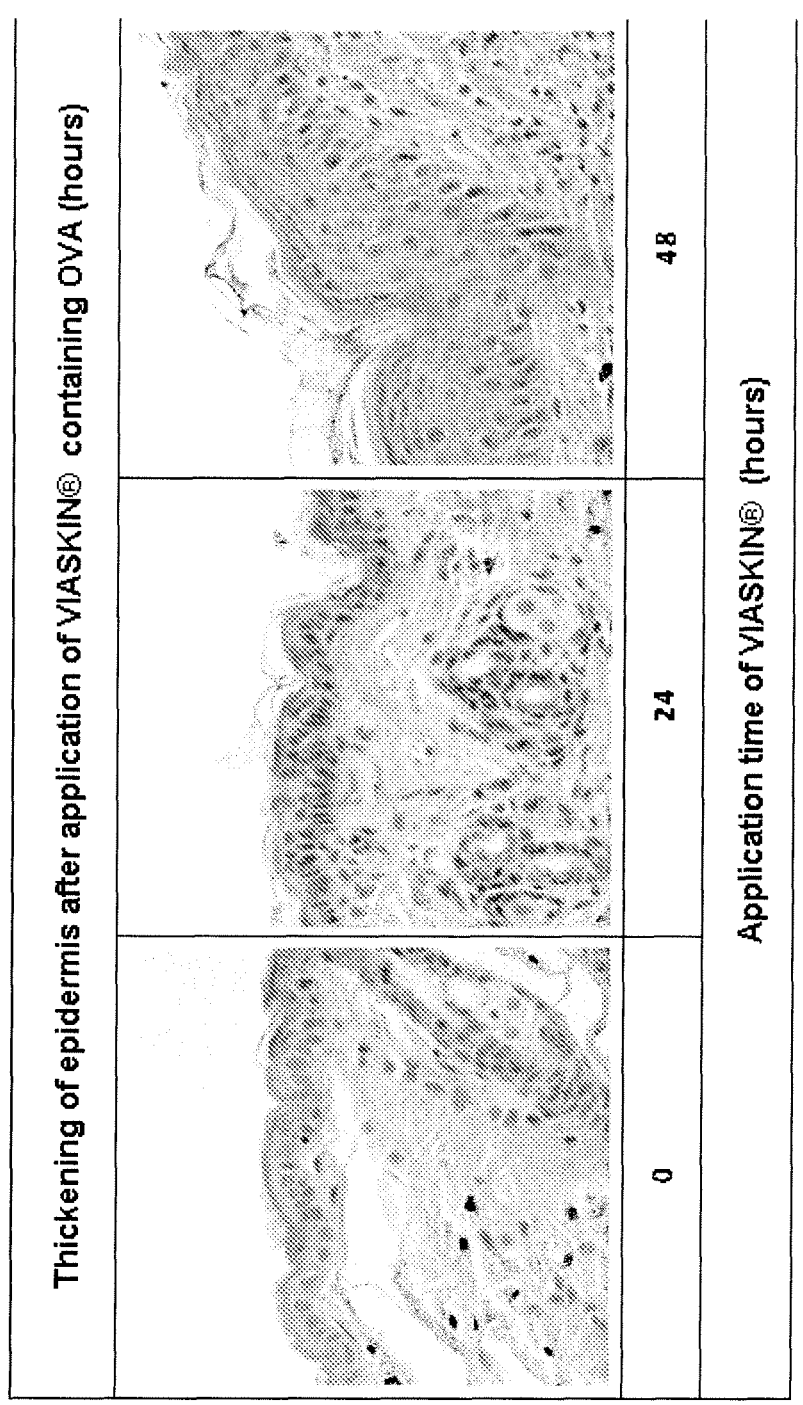
FIG. 10: Induced thickening of the epidermis, related to rupture of cutaneous homeostasis, proportional to the extension of the application time to the skin of the device with condensation compartment.

Induced Thickening of the Epidermis, Proportional to the Extension of the Application Time to the Skin of the Device with Condensation Compartment Cutaneous administration devices comprising a condensation compartment, prepared following Example 1, but with a volume of 10 mm$^3$/cm$^2$ containing OVA (100 µg/cm$^2$) in dry form, were applied for 0, 24 or 48 hours to the backs of female BALB/c mice (n=8 to 16), shaven and depilated the day before the applications. The area of skin under the condensation compartment was sampled and frozen. The skin sections obtained from the samples were stained with Hemalun-eosin. The results in FIG. 10 show the observations seen under microscope with ×200 magnification.

The results show that the application of the cutaneous administration device with condensation compartment containing OVA, induces thickening of the epidermis which is visible after 24 hours' application and major after 48 hours' application.

Example 11

Figure 11:
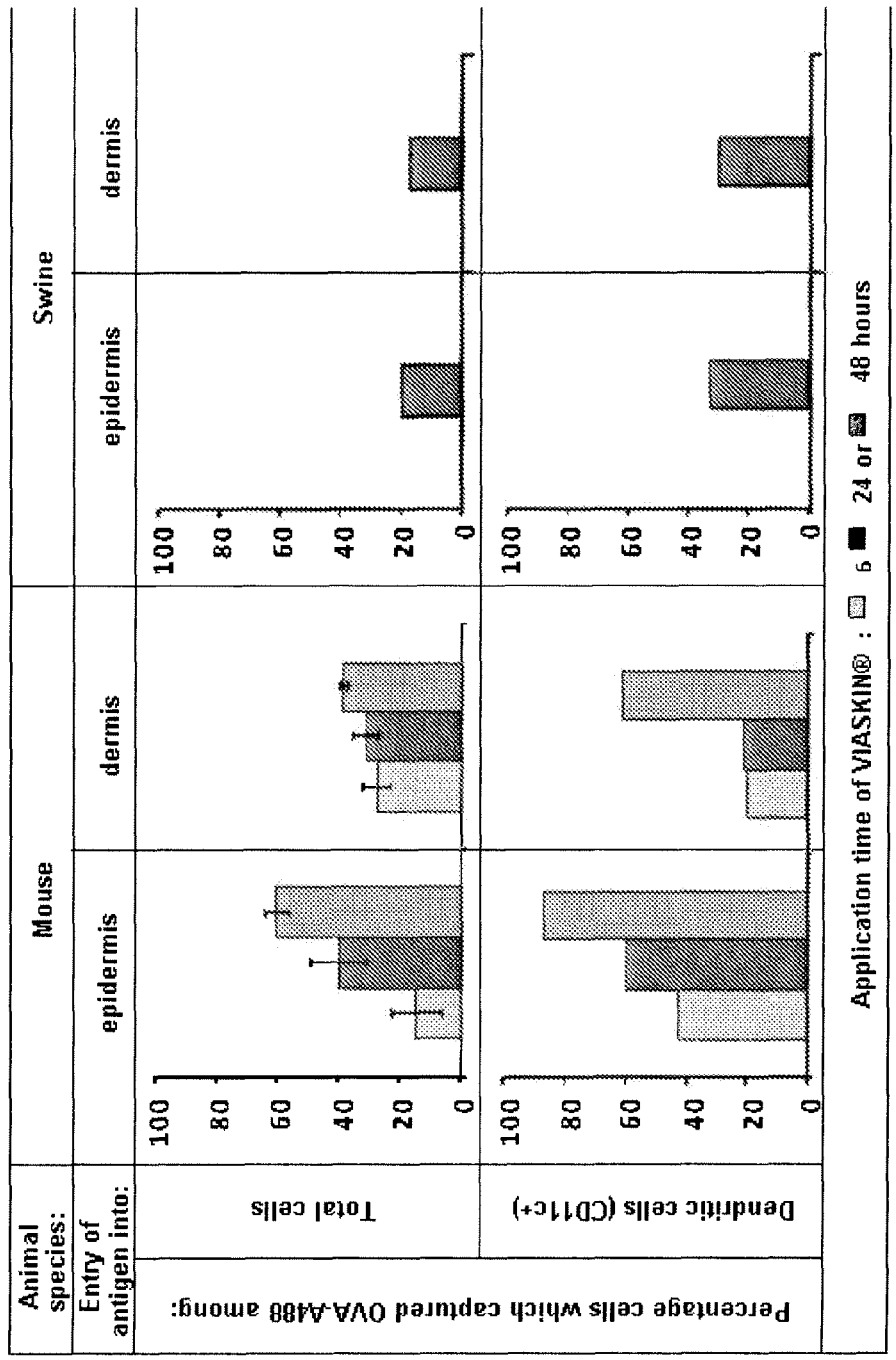
FIG. 11: Induction of antigen entry into the skin, and of its processing by the dendritic cells, proportional to the extension of the application time to the skin of the device with condensation compartment.

Induction of Entry of the Antigen into the Skin and its Processing by the Dendritic Cells, Proportional to the Extended Application Time to the Skin of the Device with Condensation Compartment Cutaneous administration devices comprising a condensation compartment prepared following Example 1 but with a volume of 10 mm$^3$/cm$^2$ containing OVA (100 µg/cm$^2$) coupled with Alexa 488 ($A_{488}$) in dry form, were applied for 6, 24 or 48 hours to the backs of female BALB/c mice (n=10 to 20), shaven and depilated the day before the applications. The area of skin under the condensation compartment was sampled. After separation of the epidermis from the dermis (0.5% trypsin), the epidermal cells were isolated by mechanical re-suspension and the dermal cells by enzymatic digestion (collagenase/DNase). OVA-$A_{488}$ was detected in the cell suspensions and among the dendritic cells, the cells being identified with CD11c marker by flow cytometry (FACscallibur and Cell quest software). The results shown in FIG. 11 are expressed as a percentage of fluorescent cells (OVA-$A_{488}^+$) among total cells and among dendritic cells (CD11c$^+$) of each cell suspension (epidermis and dermis).

The results show that some epidermal and detrital cells are OVA-$A_{488}^+$ and that their proportion increases with the extension of the application time of the cutaneous administration device with condensation compartment containing OVA-$A_{488}$. Part of these OVA-$A_{488}^+$ cells are dendritic cells (CD11c+) and similarly the percentage of dendritic OVA-$A_{488}^+$ cells increases with the extension of the application time of the cutaneous administration device comprising a condensation compartment.

Cutaneous administration devices comprising a condensation compartment prepared following Example 1 but with a volume of 10 mm$^3$/cm$^2$ containing OVA (100 µg/cm$^2$) coupled with Alexa 488 (A488) in dry form were applied for 24 hours to the back of a swine (n=1), shaven and depilated the day before the applications.

The area of skin under the condensation compartment was sampled. After separation of the epidermis from the dermis (0.5% trypsin), the epidermal cells were isolated by mechanical re-suspension and the dermal cells by enzymatic digestion (collagenase/DNase). OVA-$A_{488}$ was detected in the cell suspensions and among the dendritic cells, the cells being identified with the SLA-II marker by flow cytometry (FACscallibur and Cell quest software). The results shown in FIG. 11 are expressed as a percentage of fluorescent cells (OVA-$A_{488}^+$) among the total cells and among the dendritic cells (SLA-II$^+$) of each cell suspension (epidermal and dermal).

The results show that some epidermal and dermal cells are OVA-$A_{488}^+$ after 24 h application of the cutaneous administration device with condensation compartment containing OVA-$A_{488}$. Part of these OVA-$A_{488}^+$ cells are dendritic cells (SLA-II+).

The results given in FIG. 11 show that the cutaneous administration device comprising a condensation compartment promotes the entry of the antigen into the skin, and its processing by the dendritic cells.

Example 12

Figure 12:
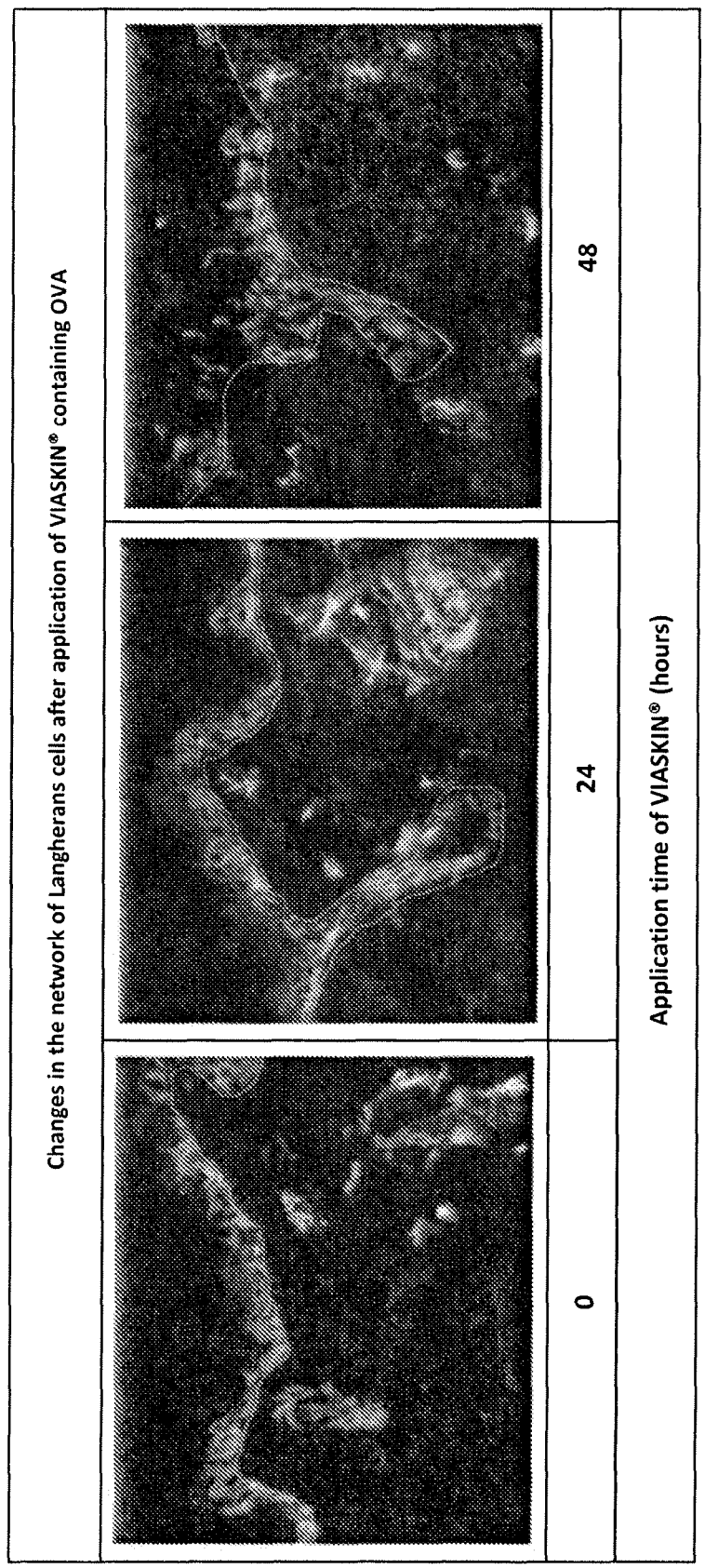
FIG. 12: Induced changes in the network of epidermal Langerhans cells, in relation to activation of these cells, proportional to the extension of the application time to the skin of the device with condensation compartment.

Induced Changes in the Network of Epidermal Langerhans Cells, Proportional to the Extension of the Application Time to the Skin of the Device with Condensation Compartment Cutaneous administration devices comprising a condensation compartment prepared following Example 1 but with a volume of 10 mm$^3$/cm$^2$ containing OVA (100 µg) in dry from were applied for 0, 24 or 48 hours to the backs of female BALB/c mice (n=5), shaven and depilated the day before the applications. The area of skin underneath the condensation compartment was sampled and frozen. The Langherans cells were identified on the skin sections obtained from the samples using a CD207 marker. The results given in FIG. 12 show the observations made under microscopy with ×200 magnification.

The results show that the application of a cutaneous administration device with condensation compartment containing OVA induces a modification in the network of Langherans cells of the epidermis, which are visible after 24 hours' application and major after 48 hours' application. This phenomenon is characteristic of activation of these cells.

Example 13

Figure 13:
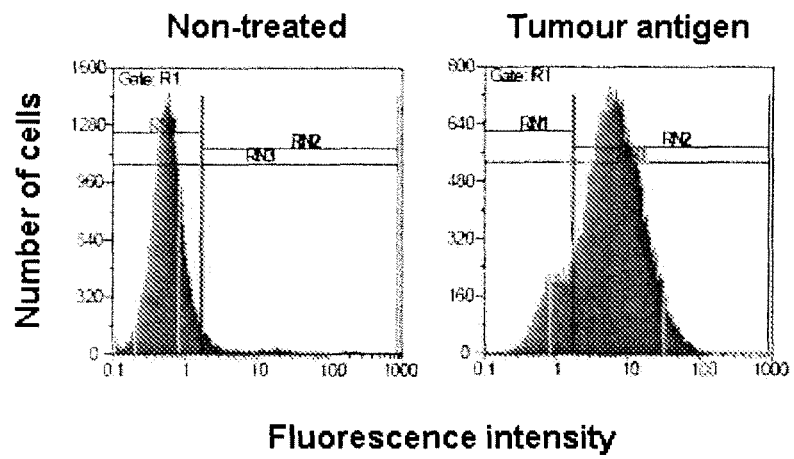
FIG. 13: Induced production of antibodies specific to a tumour antigen, capable of targeting in vitro cells which expressing this antigen after applications of 24 h to the skin of a device with condensation compartment containing the tumour antigen.

Induced Production of Antibodies Specific to a Tumour Antigen Capable of Targeting In Vitro Cells Expressing this Antigen after Application Times of 24 h to the Skin of a Device with Condensation Compartment Containing the Tumour Antigen Cutaneous administration devices comprising a condensation compartment prepared following Example 1 were prepared but with a volume of 10 mm$^3$/cm$^2$ containing a tumour antigen in dry form, were applied for 24 hours to the backs of female BALB/c mice (n=6), shaven and depilated the day before the applications. The applications were renewed at 2 and 4 weeks after the first. The anti-antigen total IgG-type antibodies were assayed by ELISA on the sera of animals sampled 2 weeks after the last application. The sera of the animals were incubated with cells expressing the tumour antigen. Fixing of the tumour anti-antigen antibodies on the cells was detected after labelling with a fluorescent, mouse anti-Ig antibody by flow cytometry (FACscallibur and Cell quest software). The results in FIG. 13 are given in the form of a histogram showing fluorescence intensity in relation to the number of cells.

The results show that the tumour anti-antigen antibodies contained in the sera of mice immunized via epicutaneous route using a cutaneous administration device with condensation compartment containing the tumour antigen, exhibit in vitro recognition of cells expressing the tumour antigen.

Example 14

Figure 14:
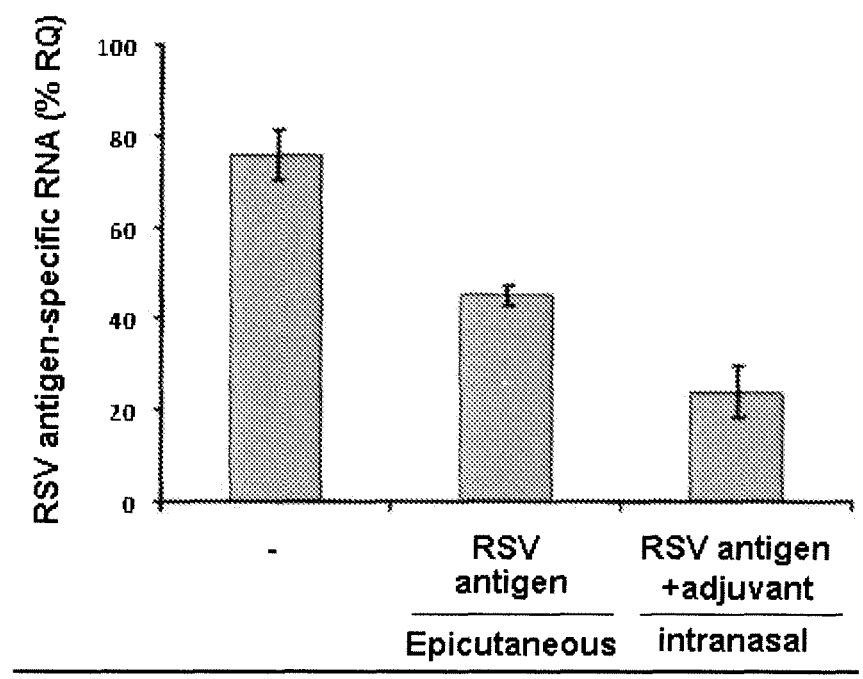
FIG. 14: Induction of partial protection against infection with the respiratory syncytial virus (RSV) in young mice after 48 h application to the skin of a device with condensation compartment containing an RSV antigen.

Induced Partial Protection Against Infection with the Respiratory Syncytial Virus (RSV) in Young Mice after 48 Hours' Application to the Skin of a Device with Condensation Compartment Containing an RSV Antigen Cutaneous administration devices comprising a condensation compartment prepared following Example 1 but with a volume of 10 mm$^3$/cm$^2$ containing an antigen of the respiratory syncytial virus in dry form, were applied for 48 hours to the backs of young BALB/c mice (7 days). The antigen was co-administered with an adjuvant via intra-nasal route for the controls. The viral test was performed 23 days after vaccination via nasal route. The assay of the viral RNAs was performed on the lungs sampled 5 days after infection. The results given in FIG. 14 are expressed in relative quantities of viral RNA in the lungs, compared with a reference gene and standardized relative to a positive control (non-vaccinated individual).

The results show that the viral load in the young mice, after 48 hours' application to the skin of a device with condensation compartment containing an RSV antigen, was reduced by one half compared with non-treated young mice.

The invention claimed is:

1. A method for the epicutaneous vaccination of a mammal against a pathogen, the method comprising:
    applying a dry vaccine formulation onto intact skin of the mammal, wherein the skin at the application site has an intact stratum corneum,
    wherein the dry vaccine formulation comprises an antigen and is devoid of an adjuvant, and
    wherein applying comprises contacting a device to the application site, the device comprising a condensation compartment having a volume ranging between 2 and 100 mm$^3$/cm$^2$ of a surface area of the device and a height between 0.02 and 1 mm, the surface area between 0.2 and 5 cm$^2$, said device containing a quantity of the dry vaccine formulation ranging between 0.1 µg and 500 µg per cm$^2$ of the surface area of the device.

2. The method of claim 1, wherein the condensation compartment comprises walls formed of a material having a moisture vapor transmission rate that is less than about 10 g/m$^2$/24 h.

3. The method of claim 1, wherein the condensation compartment increases a hydration rate of the skin in the condensation compartment by at least 50% after one hour of application.

4. The method of claim 1, further comprising adhering the device onto the application site.

5. The method of claim 1, wherein the dry vaccine formulation is in powder form.

6. The method of claim 1, wherein the dry vaccine formulation is held on a surface of the device by forces of chemical or physicochemical type, in the absence of adhesive material on this surface.

7. The method of claim 6, wherein the forces comprise electrostatic forces or Van der Waals forces.

8. The method of claim 1, wherein the dry vaccine formulation comprises at least one antigen of peptide or polypeptide type, or a polypeptide conjugate with a component of different chemical type.

9. The method of claim 1, further comprising successively applying to the mammal at least two devices, each application being spaced apart by about 7 to 30 days.

10. The method of claim 9, comprising maintaining each of the devices in contact with the skin for a period of about 6 to 72 hours.

11. The method of claim 9, comprising maintaining each of the devices in contact with the skin for a period of about 48 hours, each application being spaced apart by about 15 days.

12. The method of claim 1, wherein the antigen induces an antibody response of IgG type.

13. The method of claim 1, wherein the dry vaccine formulation further comprises, or is co-administered with, an immunomodulator compound.

14. The method of claim 1, wherein the device contains a quantity of dry vaccine formulation ranging between 20 μg and 300 μg per cm$^2$ of surface.

15. The method of claim 1, wherein the device contains a quantity of dry vaccine formulation ranging between 20 μg and 100 μg per cm$^2$ of surface.

16. The method of claim 1, further comprising successively applying to the mammal at least two devices, each application being spaced apart by about 10 to 20 days.

17. The method of claim 1, further comprising successively applying to the mammal at least two devices, each application being spaced apart by about 15 days.

18. The method of claim 9, comprising maintaining each of the devices in contact with the skin for a period of about 6 to 48 hours.

19. The method of claim 9, comprising maintaining each of the devices in contact with the skin for a period of about 48 hours.

20. The method of claim 13, wherein the immunomodulator compound is selected from a cytokine and a Toll receptor ligand.

21. The method of claim 1, wherein the pathogen is selected from a virus, a parasite, a bacterium, a protein, a tumor cell, and a self antigen.

* * * * *